United States Patent
Suzuki et al.

(10) Patent No.: US 10,274,423 B2
(45) Date of Patent: Apr. 30, 2019

(54) GAS DETECTION DEVICE, GAS DETECTION METHOD, AND GAS DETECTION PROGRAM

(71) Applicant: KONICA MINOLTA, INC., Chiyoda-ku (JP)

(72) Inventors: Akihiro Suzuki, Tokyo (JP); Motohiro Asano, Osaka (JP); Hiroshi Takahashi, Tokyo (JP)

(73) Assignee: Konica Minolta, Inc., Tokyo (JP)

( * ) Notice: Subject to any disclaimer, the term of this patent is extended or adjusted under 35 U.S.C. 154(b) by 0 days.

(21) Appl. No.: 16/072,070

(22) PCT Filed: Jan. 11, 2017

(86) PCT No.: PCT/JP2017/000612
§ 371 (c)(1),
(2) Date: Jul. 23, 2018

(87) PCT Pub. No.: WO2017/126384
PCT Pub. Date: Jul. 27, 2017

(65) Prior Publication Data
US 2019/0041322 A1 Feb. 7, 2019

(30) Foreign Application Priority Data

Jan. 21, 2016 (JP) .................. 2016-009885

(51) Int. Cl.
*G01N 21/35* (2014.01)
*G01N 21/3504* (2014.01)
(Continued)

(52) U.S. Cl.
CPC ......... *G01N 21/3504* (2013.01); *G01N 21/59* (2013.01); *G06T 1/0007* (2013.01); *G06T 5/50* (2013.01)

(58) Field of Classification Search
CPC .... G01N 21/3504; G01N 21/35; G01N 21/39; G01N 2021/3522; G06T 5/60
See application file for complete search history.

(56) References Cited

U.S. PATENT DOCUMENTS 6,750,453 B1 * 6/2004 Nelson ............... G01N 21/3504
250/338.5
6,791,888 B2 * 9/2004 Kang ................... G11C 7/1051
365/189.05
(Continued)

FOREIGN PATENT DOCUMENTS

JP 2001-349829 12/2001
JP 2005-91343 4/2005

*Primary Examiner* — Yara B Green
(74) *Attorney, Agent, or Firm* — Cozen O'Connor (57) ABSTRACT

The gas detection device according to the present invention is provided with: a first image processing unit for generating a first binary image for indicating in binary fashion the inside and outside of a first region indicating water vapor and a gas to be detected, on the basis of a first image generated using an optical filter having a first pass wavelength band including at least an absorption wavelength band of the gas; a second image processing unit for generating a second binary image indicating in binary fashion the inside and outside of a second region indicating the water vapor, on the basis of a second image generated using an optical filter having a second pass wavelength band different from the absorption wavelength band; and a third image processing unit for calculating a difference between the first binary image and the second binary image.

7 Claims, 8 Drawing Sheets

(51) Int. Cl.
*G06T 5/50* (2006.01)
*G01N 21/59* (2006.01)
*G06T 1/00* (2006.01)

(56) References Cited

U.S. PATENT DOCUMENTS

2006/0238741 A1* 10/2006 Ninomiya .................. F23N 5/24
356/5.01
2013/0113939 A1* 5/2013 Strandemar ............... G06T 5/10
348/164
2017/0363541 A1* 12/2017 Sandsten ............ G01N 21/3504
2018/0011009 A1* 1/2018 Sandsten ............ G01N 21/3504

* cited by examiner

GAS DETECTION DEVICE, GAS DETECTION METHOD, AND GAS DETECTION PROGRAM

RELATED APPLICATIONS

This is a U.S. National Phase Application under 35 USC 371 of International Application PCT/JP2017/000612 filed on Jan. 11, 2017.

This application claims the priority of Japanese application no. 2016-009885 filed Jan. 21, 2016, the entire content of which is hereby incorporated by reference.

TECHNICAL FIELD

The present invention relates to a gas detection apparatus, a gas detection method and a gas detection program that determine an area of a gas to be detected (hereinafter referred to as a "detection target gas") in a monitoring area, using infrared images.

BACKGROUND ART

Conventionally, as a gas detection apparatus such as above, for example, there is the gas monitoring apparatus described in PTL 1 indicated below.

In the gas monitoring apparatus described in PTL 1, an infrared monitoring camera takes an image of infrared rays radiated or infrared rays reflected from the monitoring area, and includes a tunable filter that can change a transmission spectrum thereof. An image processing apparatus calculates a difference between an image taken with the tunable filter adjusted so as to have a transmission peak at one of absorption bands of a particular detection target gas (hereinafter referred to as a "first image") and an image taken with the tunable filter adjusted so as to have a transmittance peak near the absorption band thereof (hereinafter referred to as a "second image"). Subsequently, the image processing apparatus generates a differential image including, as an image of the gas, a pixel area in which infrared rays radiated or infrared rays reflected from the background of the monitoring area have been absorbed by the detection target gas.

CITATION LIST

Patent Literature

PTL 1: Japanese Patent Application Laid-Open No. 2001-349829

SUMMARY OF INVENTION

Technical Problem

However, differential images in conventional gas monitoring apparatuses have the problem of containing much noise. Specifically, pixel values indicating the background may be different between a first image and a second image because of a difference in transmitted wavelengths from the tunable filter. Furthermore, a difference in background image may occur between a first image and a second image due to, e.g., a disparity between infrared monitoring cameras and/or movement of an infrared monitoring camera. When a difference is calculated between such first and second images, a problem is that pixel values indicating the background part are visualized as noise, in addition to a detection target gas in a result of the calculation.

Therefore, an object of the present invention is to provide a gas detection apparatus, a gas detection method and a gas detection program that enable noise reduction.

Solution to Problem

In order to achieve the above object, according to a first aspect of the present invention is directed to a gas detection apparatus including: a first acquisition section that acquires a first image generated using a first optical filter having a first transmission wavelength band that is a wavelength band including at least an absorption wavelength band of a gas to be detected in a monitoring area; a second acquisition section that acquires a second image generated using a second optical filter having a second transmission wavelength band, the second transmission wavelength band being a wavelength band that is different from the absorption wavelength band; a first image processing section that generates a first binary image indicating an inside and an outside of each of respective first areas indicating the gas and water vapor, by binary values, based on the first image; a second image processing section that generates a second binary image indicating an inside and an outside of a second area indicating the water vapor, by binary values, based on the second image; and a third image processing section that calculates a difference between the first binary image and the second binary image.

In order to achieve the above object, according to a second aspect of the present invention is directed to a gas detection method comprising: a first acquisition step of acquiring a first image generated using a first optical filter having a first transmission wavelength band that is a wavelength band including at least an absorption wavelength band of a gas to be detected in a monitoring area; a second acquisition step of acquiring a second image generated using a second optical filter having a second transmission wavelength band, the second transmission wavelength band being a wavelength band that is different from the absorption wavelength band; a first image processing step of generating a first binary image indicating an inside and an outside of each of respective first areas indicating the gas and water vapor, by binary values, based on the first image; a second image processing step of generating a second binary image indicating an inside and an outside of a second area indicating the water vapor, by binary values, based on the second image; and a third image processing step of calculating a difference between the first binary image and the second binary image.

In order to achieve the above object, according to a third aspect of the present invention is directed to a gas detection program for causing a computer to function as: a first acquisition section that acquires a first image generated using a first optical filter having a first transmission wavelength band that is a wavelength band including at least an absorption wavelength band of a gas to be detected in a monitoring area; a second acquisition section that acquires a second image generated using a second optical filter having a second transmission wavelength band, the second transmission wavelength band being a wavelength band that is different from the absorption wavelength band; a first image processing section that generates a first binary image indicating an inside and an outside of each of respective first areas indicating the gas and water vapor, by binary values, based on the first image; a second image processing section that generates a second binary image indicating an inside and an outside of a second area indicating the water vapor, by binary values, based on the second image; and a third image processing section that calculates a difference between the first binary image and the second binary image.

Advantageous Effects of Invention

The above aspects enable provision of a gas detection apparatus, a gas detection method and a gas detection program that enable noise reduction.

DESCRIPTION OF EMBODIMENTS

1. Embodiment 1

Gas monitoring system 1A to which a gas detection apparatus, a gas detection method and a gas detection program according to an embodiment of the present invention are applied will be described in detail below with reference to the accompanying drawings.

<<1-1. Example Configuration of Gas Monitoring System>>

Figure 1:
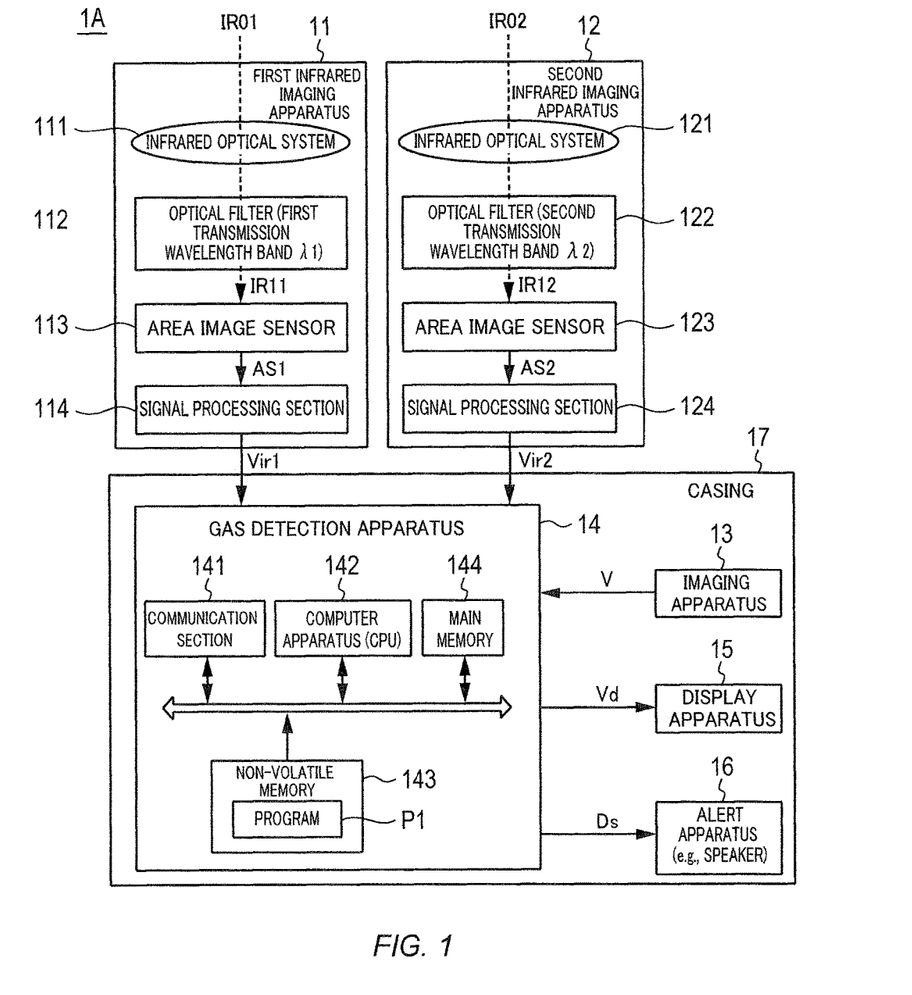
FIG. 1 is a diagram illustrating a hardware configuration of a gas monitoring system, which is an example application of a gas detection apparatus according to an embodiment of the present invention.

In FIG. 1, gas monitoring system 1A includes first infrared imaging apparatus 11, second infrared imaging apparatus 12, imaging apparatus 13, gas detection apparatus 14, display apparatus 15 and alert apparatus 16. In the present embodiment, gas detection apparatus 14, display apparatus 15 and alert apparatus 16 are housed inside same casing 17, and first infrared imaging apparatus 11, second infrared imaging apparatus 12 and imaging apparatus 13 are connected to gas detection apparatus 14 via any of a communication network, a wired transmission channel and a radio link.

Infrared imaging apparatuses 11, 12 are installed at respective positions from which an area to be monitored for leakage of a gas invisible to the naked eye (hereinafter referred to as a "detection target gas") (hereinafter referred to as a "monitoring area") can be observed. It is preferable that infrared imaging apparatuses 11, 12 be installed adjacent to each other to reduce a disparity therebetween. Infrared imaging apparatuses 11, 12 include infrared optical systems 111, 121, optical filters 112, 122, area image sensors (two-dimensional image sensors) 113, 123 and signal processing sections 114, 124, respectively.

Infrared optical systems 111, 121 output infrared rays IR01, IR02 radiated from the monitoring area, which is a subject, to optical filters 112, 122 in order to form images on area image sensors 113, 123, respectively.

Optical filter 112 is disposed on an optical path between infrared optical system 111 and area image sensor 113, and has first transmission wavelength band $\lambda 1$ that is a wavelength band including at least an absorption wavelength band of the detection target gas. Optical filter 112 lets infrared rays IR11 through, infrared rays IR11 being included in first transmission wavelength band $\lambda 1$, from among infrared rays IR01 passed through infrared optical system 111. Here, if infrared rays IR01 are ones passed through the detection target gas, no components in the absorption wavelength band of the detection target gas enter optical filter 112. Conversely, if no detection target gas exists in the monitoring area, infrared rays IR01 contain components in the absorption wavelength band of the detection target gas. Based on whether or not there are components in the absorption wavelength band, gas monitoring system 1A detects whether or not the detection target gas exists. For example, where first transmission wavelength band $\lambda 1$ is a medium wavelength band of 3.2 μm to 3.4 μm, gases indicated in the right side of the upper part of Table 1 can be detected. Also, where first transmission wavelength band $\lambda 1$ is a long wavelength band, gases indicated in the right side of the lower part of Table 1 can be detected.

TABLE 1

First transmission wavelength bands and detection target gas types

| First transmission wavelength band $\lambda 1$ | Detection target gases |
|---|---|
| 3.2 μm to 3.4 μm | butane gas |
| | methyl ethyl ketone |
| | benzene |
| | ethane |
| | methyl isobutyl ketone |
| | ethanol |
| | methane |
| | octane |
| | ethyl benzene |
| | propane |
| | pentane |
| | heptane |
| | ethylene |
| | 1-pentane |
| | hexane |
| | propylene |
| | toluene |
| | isoprene |
| | xylene |
| | methanol |
| 10 μm to 11 μm | SF6 (sulfur hexafluoride) |
| | anhydrous ammonia |
| | ethyl cyanoacrylate |
| | chlorine dioxide |
| | acetic acid |
| | CFC-12 |
| | ethylene |
| | methyl ethyl ketone (MEK) |

Optical filter 122 is disposed on an optical path between infrared optical system 121 and area image sensor 123, and lets infrared rays IR12 through, infrared rays IR12 being included in second transmission wavelength band $\lambda 2$ from among infrared rays IR02 passed through infrared optical system 121. Here, second transmission wavelength band $\lambda 2$ is set outside of first transmission wavelength band $\lambda 1$. Preferably, second transmission wavelength band $\lambda 2$ is adjacent to first transmission wavelength band $\lambda 1$ with no overlap therebetween. For example, if first transmission wavelength band $\lambda 1$ has a range of 3.2 μm to 3.4 μm, second transmission wavelength band λ2 is set to have a range of 3.5 μm to 3.7 μm. Also, if first transmission wavelength band λ1 has a range of 10 μm to 11 μm, second transmission wavelength band λ2 is set to have a range of 12 μm to 13 μm.

Area image sensors 113, 123 perform photoelectric conversion of infrared rays IR11, IR12 passed through optical filters 112, 122 to generate electric analog signals AS1, AS2 representing infrared images (thermal images) of the monitoring area, and output electric analog signals AS1, AS2, respectively. A principle of operation and a material of area image sensors 113, 123 are properly selected according to first transmission wavelength band λ1. More specifically, if first transmission wavelength band λ1 ranges from 3.2 μm to 3.4 μm, a sensor such as a cooled indium antimonide image sensor is used, and if first transmission wavelength band λ1 ranges 10 μm to 11 μm, a sensor such as a cooled QWIP (quantum well infrared detector element) is used.

In the below, the description will be continued assuming that the detection target gas is methane.

Signal processing sections 114, 124 receive analog signals AS1, AS2 from area image sensors 113, 123, convert analog signals AS1, AS2 into digital signals and thereby generate infrared moving images Vir1, Vir2, respectively. At this time, signal processing sections 114, 124 may perform known image processing as necessary. Signal processing sections 114, 124 sequentially output generated infrared moving images Vir1, Vir2 to gas detection apparatus 14 via the communication network at a predetermined frame rate, respectively. Here, infrared moving images Vir1, Vir2 are respective examples of a first infrared image and a second infrared image, and represent infrared energy radiated from the monitoring area, for example, with a 256-level gray scale.

Imaging apparatus 13 is installed at a position from which the monitoring area can be observed, near infrared imaging apparatuses 11, 12. Imaging apparatus 13 takes a moving image V (or a still image) representing the monitoring area, moving image V (or the still image) being formed of visible image frames (or a visible image frame), and transfers moving image V (or the still image) to gas detection apparatus 14 via, e.g., the communication network.

Gas detection apparatus 14 includes communication section 141, CPU 142, which is a typical example of a computer apparatus, non-volatile memory 143 and main memory 144.

Communication section 141 is a communication interface between gas detection apparatus 14 and other apparatuses 11, 12, 13, 15, 16.

Figure 2:
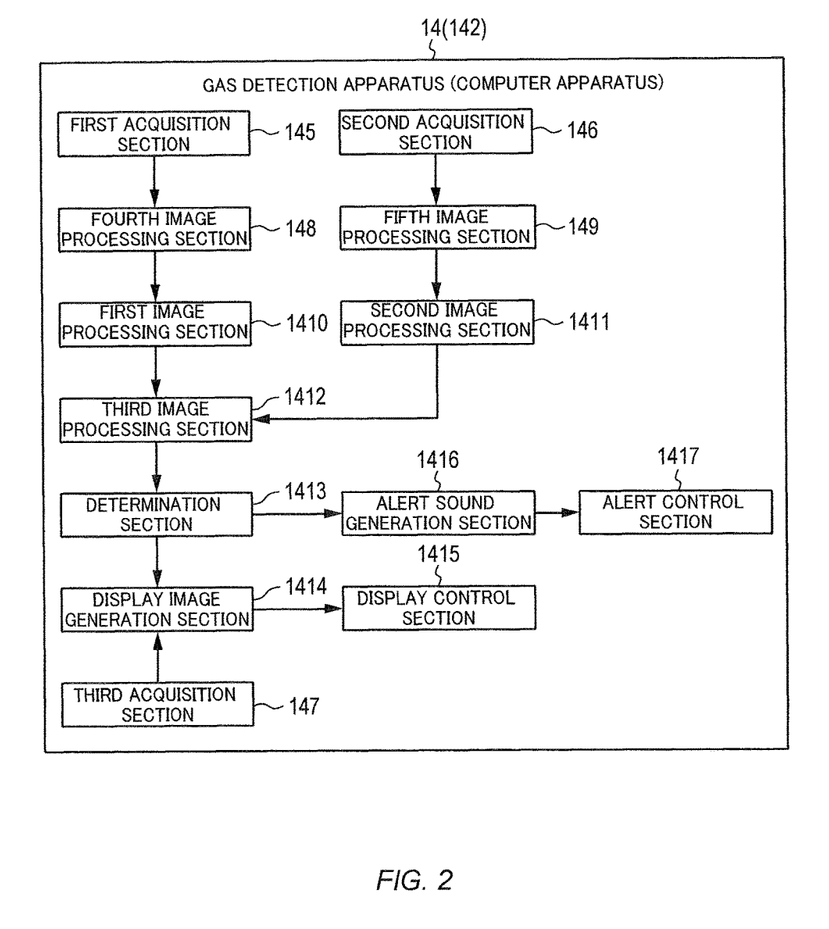
FIG. 2 is a function block diagram illustrating the computer apparatus in FIG. 1.

CPU 142 executes program P1 stored in advance in non-volatile memory 143, using main memory 144 as a work area. Consequently, as illustrated in FIG. 2, CPU 142 functions as first acquisition section 145, second acquisition section 146, third acquisition section 147, fourth image processing section 148, fifth image processing section 149, first image processing section 1410, second image processing section 1411, third image processing section 1412, determination section 1413, display image generation section 1414, display control section 1415, alert sound generation section 1416 and alert control section 1417.

Display apparatus 15 is, for example, a liquid-crystal display, and displays display image Vd generated by gas detection apparatus 14.

Alert apparatus 16 is, for example, a speaker, and outputs alert sound Ds generated by gas detection apparatus 14.

<<1-2. Operation of Gas Monitoring System>>

Next, operation of gas monitoring system 1A will be described, in particular, with operation of gas detection apparatus 14 focused on, with reference to, e.g., FIG. 3.

Figure 3:
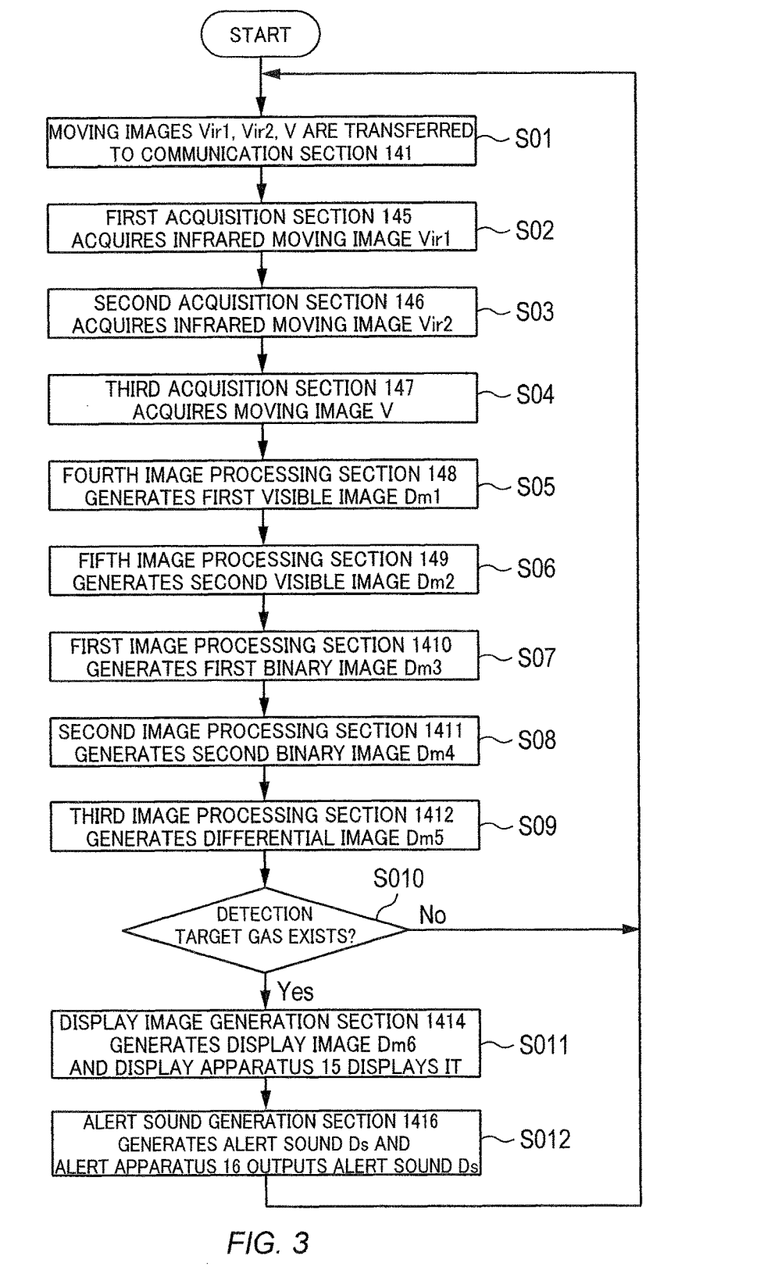
FIG. 3 is a flowchart illustrating operation of a gas monitor according to Embodiment 1, the flowchart indicating a procedure of a gas visualization method and a gas visualization program according to Embodiment 1.

First, in step S01 in FIG. 3, respective frames forming infrared moving images Vir1, Vir2 and moving image V are sequentially transferred to communication section 141 of gas detection apparatus 14.

In next steps S02, S03, first acquisition section 145 and second acquisition section 146 (CPU 142) sequentially store infrared moving images Vir1, Vir2 transferred to communication section 141, in main memory 144 on a frame-by-frame basis, respectively. Consequently, acquisition sections 145, 146 acquire infrared moving images Vir1, Vir2, respectively.

In next step S04, third acquisition section 147 sequentially stores moving image V in main memory 144 on a frame-by-frame basis.

In next step S05, fourth image processing section 148 (CPU 142) detects moving objects from each frame included in infrared moving image Vir1 by means of a background differencing technique or an optical-flow technique, and generates first visible image Dm1.

Figure 4:
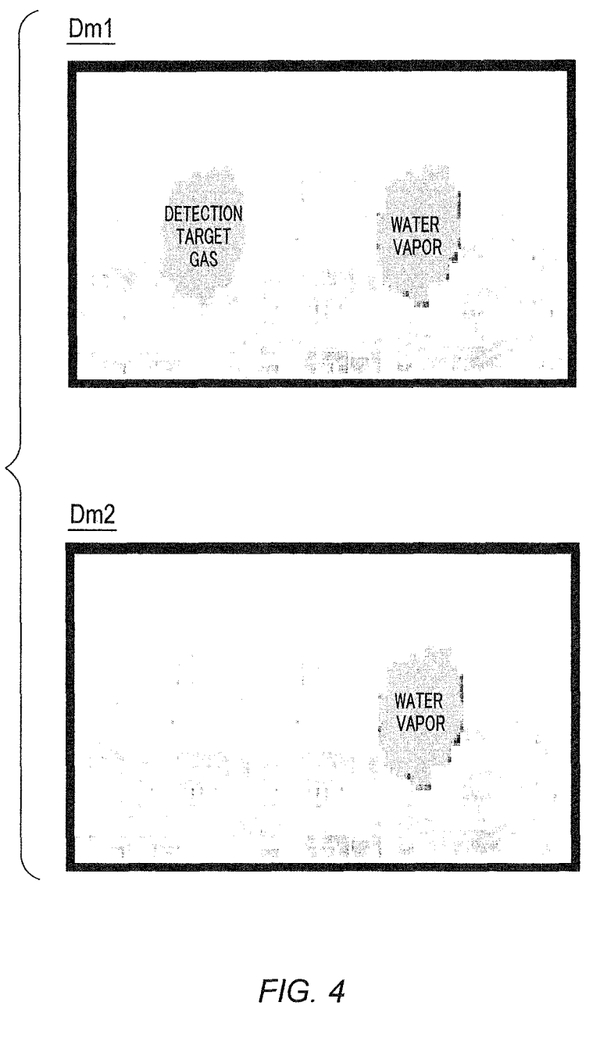
FIG. 4 is a diagram illustrating a first visible image and a second visible image.

In the background differencing technique, a first reference image taken by infrared imaging apparatus 11 in a state in which neither the detection target gas nor water vapor exists in the monitoring area is stored in advance in, e.g., non-volatile memory 143. Fourth image processing section 148 calculates a difference between each frame included in infrared moving image Vir1 and the first reference image to generate first visible image Dm1 in which the moving object in the monitoring area is visualized. Here, optical filter 121 has first transmission wavelength band λ1 including the absorption wavelength band of the detection target gas, and thus, if the detection target gas exists in the monitoring area, as illustrated in the upper part of FIG. 4, the detection target gas is visualized as a moving object in first visible image Dm1. Also, water vapor partly absorbs infrared rays radiated from the background, but re-radiates infrared rays in a wide band depending on, e.g., the temperature of the water vapor. Therefore, if water vapor exists, optical filter 121 lets infrared rays through, the infrared rays being included in the transmission wavelength band of optical filter 121 from among the infrared rays radiated by the water vapor. Therefore, in first visible image Dm1, water vapor is also visualized as a moving object.

In the optical-flow technique, fourth image processing section 148 vectorially estimates movements of moving objects in the monitoring area, using the plurality of frames forming infrared moving image Vir1. Therefore, as in the above, if the detection target gas and/or water vapor exist in the monitoring area, the detection target gas and/or the water vapor are visualized as moving object(s) in first visible image Dm1.

In next step S06, with a method similar to that of fourth image processing section 148, fifth image processing section 149 (CPU 142) detects moving objects from each frame included in infrared moving image Vir2 and generates second visible image Dm2. Here, infrared moving image Vir2 is generated using optical filter 122 having transmission wavelength band λ2. Therefore, even if the detection target gas exists in the monitoring area, as illustrated in the lower part of FIG. 4, in second visible image Dm2, the detection target gas is not visualized as a moving object. However, water vapor is visualized also in second visible image Dm2 for a reason that is similar to the above.

Here, in each of steps S05, S06, it is preferable that an absolute value of the difference be calculated in order to respond to high-temperature water vapor or low-temperature water vapor.

Figure 5:
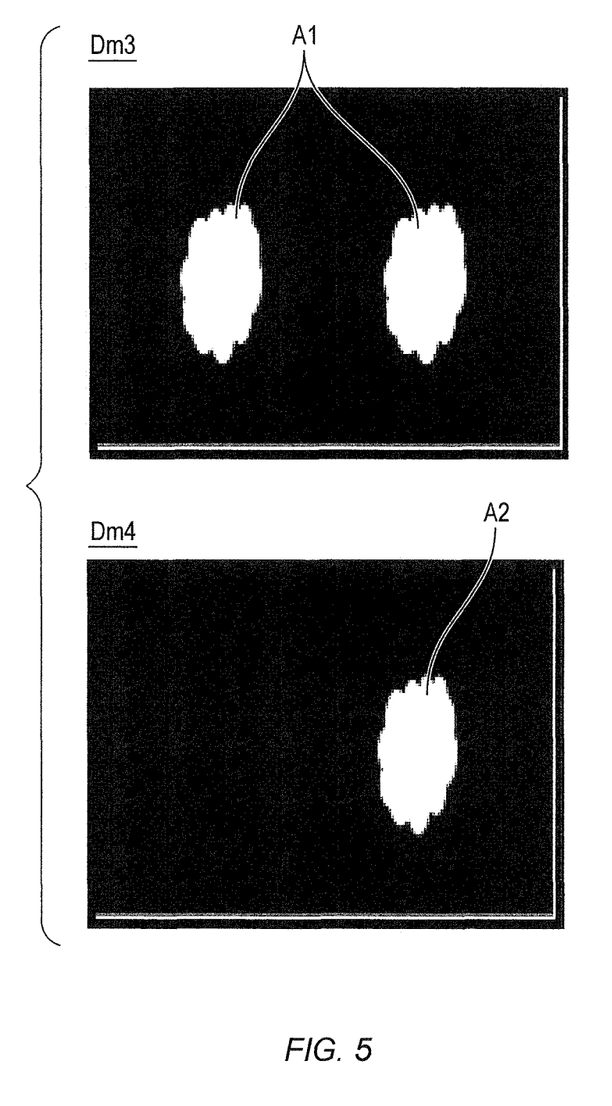
FIG. 5 is a diagram illustrating a first binary image and a second binary image.

In next step S07, first image processing section 1410 (CPU 142) performs binarization processing of first visible image Dm1 to generate first binary image Dm3. More specifically, in first visible image Dm1, each pixel value indicating any of the detection target gas and water vapor has, for example, a large value. On the other hand, since first visible image Dm1 is generated by means of, e.g., the background differencing technique, in first visible image Dm1, each pixel value indicating a background part of the detection target gas and the water vapor has a relatively small value. In program P1, a threshold value for distinguishing between the detection target gas and the water vapor, and the background part is derived in advance by, e.g., tests conducted at the design and development stage of gas detection apparatus 14. First image processing section 1410 compares each pixel value of first visible image Dm1 with the threshold value to set values of all of the pixels indicating the detection target gas and the water vapor to, for example, either one of "0" and "255" and set values of all of the pixels indicating the background part to the other. As a result of the above processing, as illustrated in the upper part in FIG. 5, first binary image Dm3 indicating the inside of each of respective first pixel areas A1 indicating the detection target gas and the water vapor and the outside of each of the first pixel areas A1, the outside indicating the background part, by binary values, is generated.

In next step S08, second image processing section 1411 (CPU 142) performs binarization processing of second visible image Dm2 to generate second binary image Dm4. This processing is performed in a manner that is the same as that in step S07. As a result, as illustrated in the lower part of FIG. 5, second binary image Dm4 indicating the inside of second pixel area A2 indicating the water vapor and the outside of second pixel area A2, the outside indicating the background part, by binary values, is generated.

Figure 6:
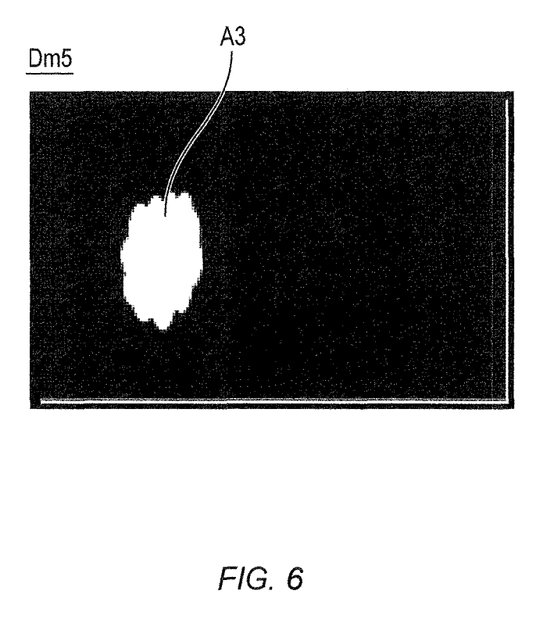
FIG. 6 is a diagram illustrating a differential image.

In next step S09, third image processing section 1412 (CPU 142) calculates a difference between first binary image Dm3 and second binary image Dm4. If the detection target gas exists in the monitoring area, as illustrated in FIG. 6, the calculated difference is differential image Dm5 indicating the inside of third pixel area A3 indicating the detection target gas and the outside of the third pixel area A3, the outside being a part other than the detection target gas, by binary values.

In next step S010, determination section 1413 determines whether or not any pixel value indicating the detection target gas (that is, either one of "0" and "255") exists in differential image Dm5. If determination section 1413 makes determination of Yes, determination section 1413 considers the detection target gas as existing in the monitoring area, and performs steps S010, S011. On the other hand, if determination section 1413 makes determination of No, determination section 1413 considers no detection target gas as existing and returns to S01 without performing steps S010, S011.

In step S011, display image generation section 1414 superimposes differential image Dm5 for each frame of moving image V on the frame to generates display moving image Vd. Subsequently, display control section 1415 transfers display moving image Vd to display apparatus 15, and display apparatus 15 displays received moving image Vd. A user views moving image Vd and thereby recognizes leakage of the detection target gas in the monitoring area.

Also, in step S012, alert sound generation section 1416 generates alert sound Ds, and alert apparatus 16 outputs generated alert sound Ds under the control of alert sound control section 1417. The output of alert sound Ds also enables the user to recognize leakage of the detection target gas in the monitoring area.

<<1-3. Effects>>

As above, in steps S07, S08, CPU 142 generates binary images Dm3, Dm4, respectively. In binary images Dm3, Dm4, pixel areas A1, A2 indicating the background part are subjected to replacement so as to have a single value. Therefore, noise is less likely to occur in the background part of differential image Dm5 generated based on binary images Dm3, Dm4. In other words, differential image Dm5 can clearly define third pixel area A3 indicating the detection target gas.

Also, in step S010, CPU 142 can correctly determine whether or not the detection target gas exists because of use of differential image Dm5 described above.

Also, in step S011, CPU 142 superimposes differential image Dm5 on moving image V, and thus, low-noise display moving image Vd is displayed on display apparatus 15. Accordingly, a user can correctly determine whether or not the detection target gas exists, by viewing display moving image Vd.

Also, in step S010, CPU 142 can correctly determine whether or not the detection target gas exists, and thus the user can also correctly determine whether or not the detection target gas exists, based on alert sound Ds.

<<1-4. Alteration>>

Figure 7:
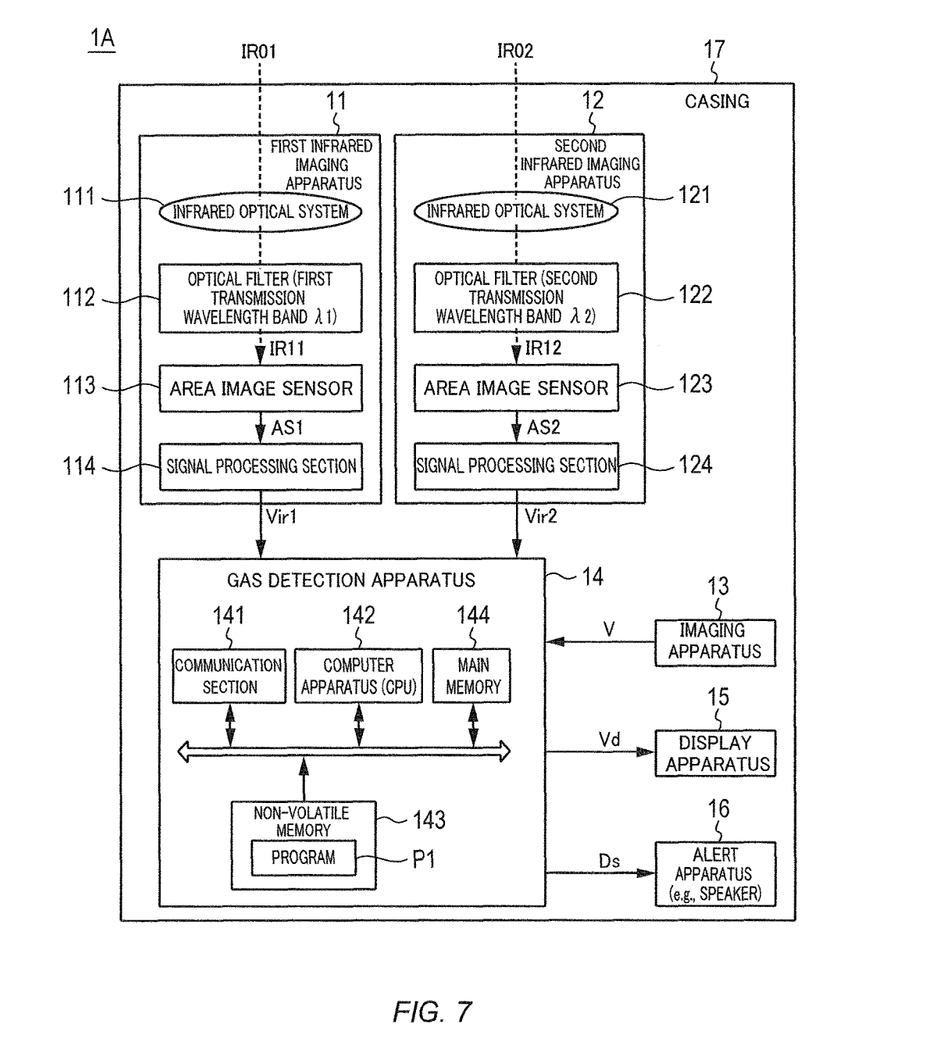
FIG. 7 is a diagram illustrating a hardware configuration of a gas monitoring system according to a first alteration.
Figure 8:
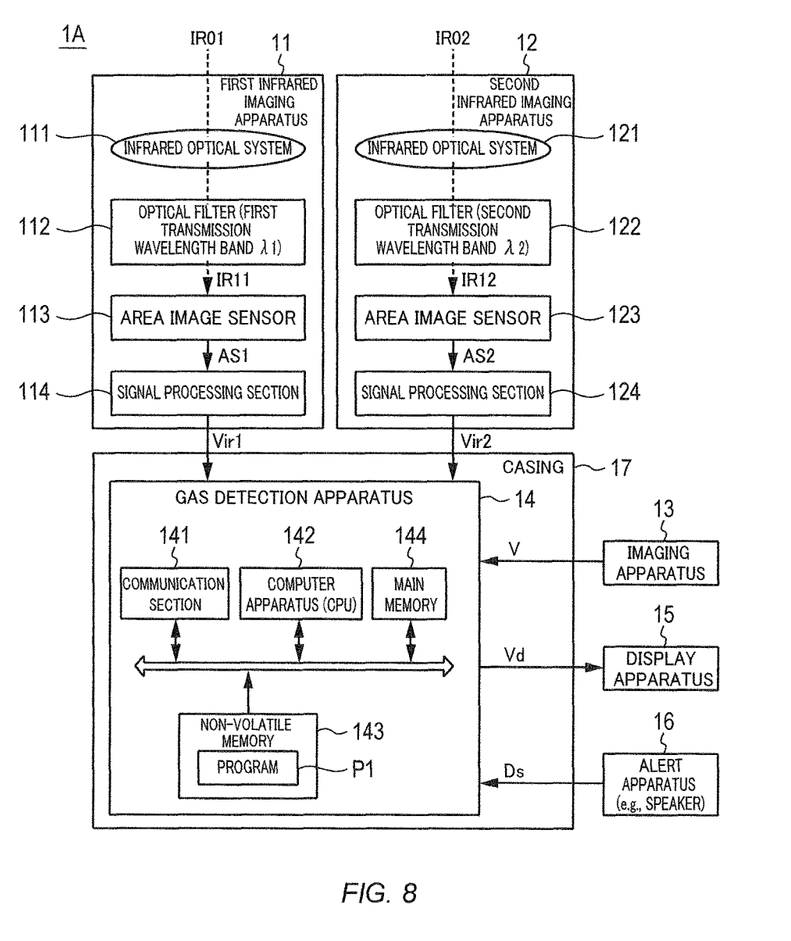
FIG. 8 is a diagram illustrating a hardware configuration of a gas monitoring system according to a second alteration.

Gas monitoring system 1A in FIG. 1 has been described as one in which: first infrared imaging apparatus 11, second infrared imaging apparatus 12 and imaging apparatus 13 are connected to gas detection apparatus 14 via a communication network; and gas detection apparatus 14, display apparatus 15 and alert apparatus 16 are incorporated in same casing 17. However, the present invention is not limited to this example, and as illustrated in FIG. 7, gas monitoring system 1A may incorporate first infrared imaging apparatus 11, second infrared imaging apparatus 12, imaging apparatus 13, gas detection apparatus 14, display apparatus 15 and alert apparatus 16 in same casing 17. Also, as illustrated in FIG. 8, gas detection apparatus 14 may be connected to each of first infrared imaging apparatus 11, second infrared imaging apparatus 12, imaging apparatus 13, display apparatus 15 and alert apparatus 16 via a communication network. Here, in each of the cases in FIGS. 7 and 8, operation and processing in each component are as described above.

<<1-5. Supplement 1>>

The above embodiment has been described in terms of the case where gas monitoring system 1A includes second infrared imaging apparatus 12. As described above, it is sufficient that second infrared imaging apparatus 12 includes optical filter 122 having transmission wavelength band $\lambda 2$ outside of absorption wavelength band $\lambda 1$. Here, transmission wavelength band $\lambda 2$ is not limited to an infrared wavelength band. In other words, gas monitoring system 1A may include an imaging apparatus that can take a visible image, instead of second infrared imaging apparatus 12.

<<1-6. Supplement 2>>

The above embodiment has been described in terms of the case where alert apparatus 16 is a speaker that outputs alert sound Ds. However, the present invention is not limited to this case, alert apparatus 16 may alert a user to existence of a detection target gas by means of light or vibration.

<<1-7. Supplement 3>>

The above embodiment has been described in terms of the case where gas monitoring system 1A includes two infrared imaging apparatuses 11, 12. However, functions similar to those of two infrared imaging apparatuses 11, 12 can be provided by a single infrared imaging apparatus alone. In other words, this infrared imaging apparatus selectively switches between optical filters 112 and 122 to generate infrared moving images Vir1, Vir2 time-divisionally, and transfers infrared moving images Vir1, Vir2 to gas detection apparatus 14.

<<1-8. Supplement 4>>

Also, program P1 described above may be provided not only in a state in which program P1 is stored in non-volatile memory 123, but also via a recording medium such as a DVD (digital versatile disc) or a communication network.

The entire disclosure of the description, the drawings and the abstract included in Japanese Patent Application No. 2016-009885 filed on Jan. 21, 2016 is incorporated herein.

INDUSTRIAL APPLICABILITY

The gas detection apparatus, the gas detection method and the gas detection program according to the present invention enable noise reduction and are thus suitable for, e.g., a gas monitoring system.

REFERENCE SIGNS LIST 1A gas monitoring system
11 first infrared imaging apparatus
12 second infrared imaging apparatus
13 imaging apparatus
14 gas detection apparatus
142 computer apparatus (CPU)
P1 program
145 first acquisition section
146 second acquisition section
1410 first image processing section
1411 second image processing section
1412 third image processing section
1413 determination section
15 display apparatus
16 alert apparatus

The invention claimed is:

1. A gas detection apparatus comprising:
a hardware processor that:
acquires a first image generated using a first optical filter having a first transmission wavelength band that is a wavelength band including at least an absorption wavelength band of a gas to be detected in a monitoring area;
acquires a second image generated using a second optical filter having a second transmission wavelength band, the second transmission wavelength band being a wavelength band that is different from the absorption wavelength band;
generates a first binary image indicating an inside and an outside of each of respective first areas indicating the gas and water vapor, by binary values, based on the first image;
generates a second binary image indicating an inside and an outside of a second area indicating the water vapor, by binary values, based on the second image; and
calculates a difference between the first binary image and the second binary image.

2. The gas detection apparatus according to claim 1, wherein the hardware processor determines whether or not the gas exists in the monitoring area, based on the difference.

3. The gas detection apparatus according to claim 1, further comprising a display apparatus that displays a display image in which a third area indicating the gas is visualized based on the difference.

4. The gas detection apparatus according to claim 1, further comprising an alert apparatus that provides alert of existence of the gas in the monitoring area, based on the difference.

5. The gas detection apparatus according to claim 1, wherein the hardware processor defines the first areas and the second area based on either of a background differencing technique and an optical-flow technique.

6. A gas detection method comprising:
acquiring a first image generated using a first optical filter having a first transmission wavelength band that is a wavelength band including at least an absorption wavelength band of a gas to be detected in a monitoring area;
acquiring a second image generated using a second optical filter having a second transmission wavelength band, the second transmission wavelength band being a wavelength band that is different from the absorption wavelength band;
generating a first binary image indicating an inside and an outside of each of respective first areas indicating the gas and water vapor, by binary values, based on the first image;
generating a second binary image indicating an inside and an outside of a second area indicating the water vapor, by binary values, based on the second image; and
calculating a difference between the first binary image and the second binary image.

7. A gas detection program for causing a computer to perform:
acquiring a first image generated using a first optical filter having a first transmission wavelength band that is a wavelength band including at least an absorption wavelength band of a gas to be detected in a monitoring area;
acquiring a second image generated using a second optical filter having a second transmission wavelength band, the second transmission wavelength band being a wavelength band that is different from the absorption wavelength band;
generating a first binary image indicating an inside and an outside of each of respective first areas indicating the gas and water vapor, by binary values, based on the first image;
generating a second binary image indicating an inside and an outside of a second area indicating the water vapor, by binary values, based on the second image; and
calculating a difference between the first binary image and the second binary image.

* * * * *